(12) United States Patent
Inoue et al.

(10) Patent No.: US 6,747,185 B2
(45) Date of Patent: Jun. 8, 2004

(54) DISPOSABLE UNDERGARMENT WITH URINATION INDICATOR

(75) Inventors: Yasushi Inoue, Kagawa-ken (JP); Naoto Ohashi, Kagawa-ken (JP); Takayuki Miyoshi, Kagawa-ken (JP); Toshiyasu Yoshioka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 86 days.

(21) Appl. No.: 10/043,941

(22) Filed: Jan. 11, 2002

(65) Prior Publication Data
US 2002/0095126 A1 Jul. 18, 2002

(30) Foreign Application Priority Data
Jan. 12, 2001 (JP) ......................... 2001-005600

(51) Int. Cl.[7] ............................. A61F 13/15; A61F 13/20
(52) U.S. Cl. ......................... 604/361; 604/367
(58) Field of Search ..................... 604/361, 362, 604/364, 367

(56) References Cited

U.S. PATENT DOCUMENTS

| 6,140,551 A | 10/2000 | Niemeyer et al. | |
| 2001/0031954 A1 * | 10/2001 | Jordan et al. | 604/385.01 |
| 2001/0044611 A1 * | 11/2001 | Noda et al. | 604/367 |

FOREIGN PATENT DOCUMENTS

| EP | 1 078 620 A2 | 2/2001 |
| EP | 1 147 755 A2 | 10/2001 |
| EP | 0 776 645 B1 | 3/2002 |
| JP | 1997-140742 A | 6/1997 |
| WO | WO 99/60973 | 12/1999 |

* cited by examiner

Primary Examiner—Kim M. Lewis
Assistant Examiner—Michele Kidwell
(74) Attorney, Agent, or Firm—Butzel Long

(57) ABSTRACT

A disposable undergarment that includes a liquid-impervious base sheet and a liquid-absorbent structure lying on a wearer's skin side surface of the base sheet. The base sheet includes a breathable but liquid-impervious plastic film and a fibrous nonwoven fabric joined to the plastic film to define an undergarment side surface, the base sheet having a total luminous transmittance in a range between 60 and 85%.

7 Claims, 5 Drawing Sheets

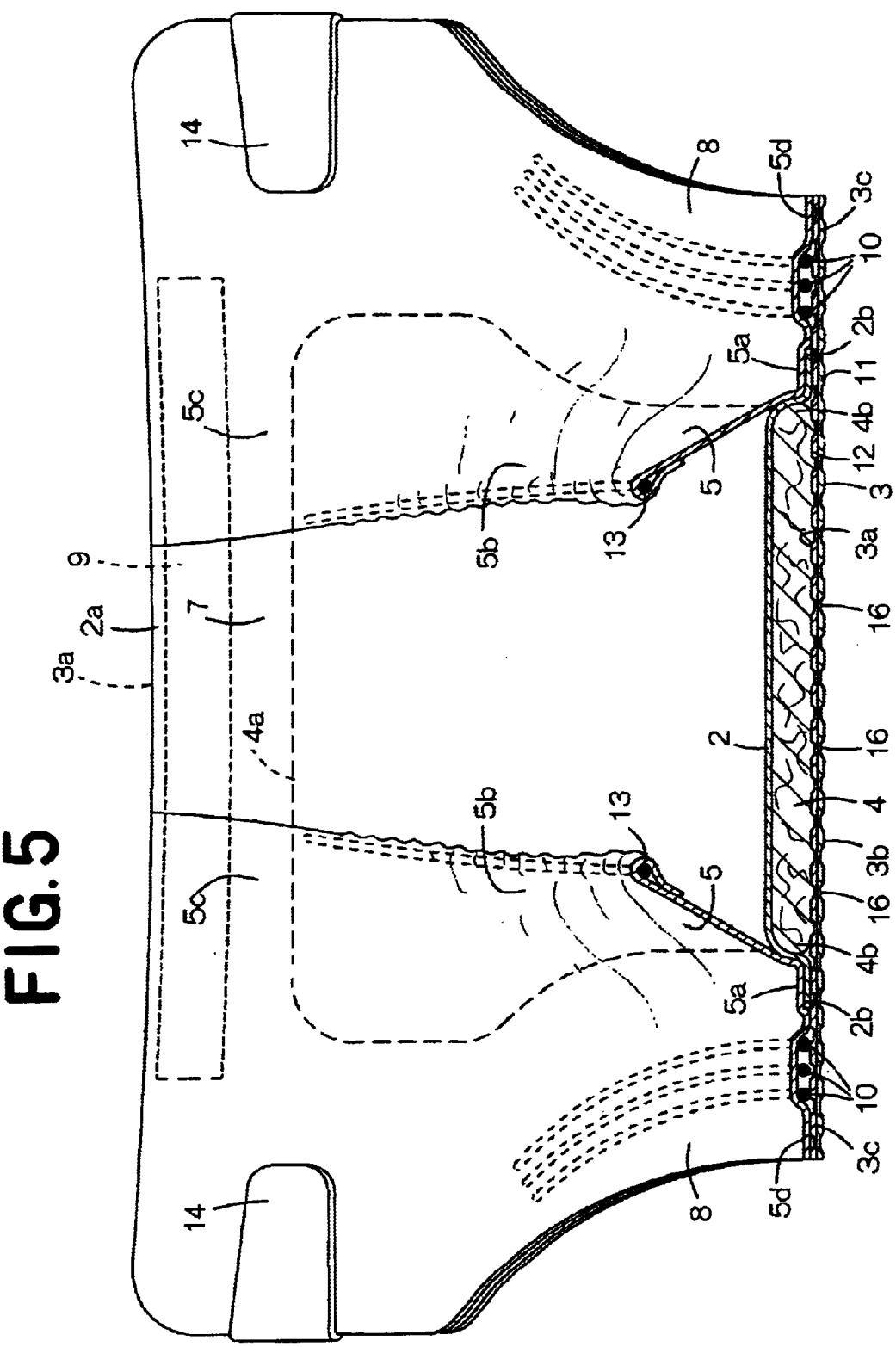

DISPOSABLE UNDERGARMENT WITH URINATION INDICATOR

BACKGROUND OF THE INVENTION

This invention relates to a disposable undergarment adapted to absorb body exudates and to retain them.

Japanese Patent Application Publication No. 1997-140742A discloses a disposable diaper comprising a liquid-pervious topsheet, a liquid-impervious base sheet and a liquid-absorbent core disposed between these sheets wherein a front or a rear waist region of the diaper is provided with an indicator enabling a caretaker to detect whether urination has occurred or not from the exterior.

The indicator comprises a hydrophilic substrate sheet, a first coating layer printed on one side of the surface of the substrate sheet so that its initial color becomes distinct as it is wetted with urine, and a second coating layer printed on the first coating layer so that it normally conceals the first coating layer but becomes transparent as it is wetted with urine. The substrate sheet is formed by breathable but a liquid-impervious film obtained by stretching a plastic film containing particles of inorganic fillers such as titanium dioxide, barium sulfate or calcium carbonate. The substrate sheet has white or milky white color and a luminous transmittance in a range between 30 and 70%.

With this diaper, the indicator is intermittently bonded to the surface of the base sheet facing the wearer's skin. A pattern defined by the first coating layer becomes distinct and the second coating layer becomes transparent as the indicator is wetted with urine. The pattern is distinctly vidible from the side facing away from the wearer's skin so that occurrence of urination can be visually recognized by the helper from the exterior.

The above-cited Publication discloses one example of the base sheet formed by a composite sheet consisting of the plastic film and a fibrous nonwoven fabric bonded to this plastic film so that the plastic film defines the surface facing the wearer's skin and the nonwoven fabric defines the surface facing away from the wearer's skin. With the diaper using such a composite sheet as the base sheet, a feeling of touch with the base sheet is more or less improved but a luminous transmittance of the base sheet is reduced by the fibrous nonwoven fabric in comparison to the base sheet formed by the plastic film alone. No description on the luminous transmittance of the composite sheet is found in the above-cited Publication. Depending on the luminous transmittance of the composite sheet, there is a possibility that the pattern might be concealed by the base sheet and it might be difficult for the helper to visually recognize the pattern from the side of the base sheet even when the pattern is wetted with urine and the pattern itself becomes distinct. Additionally, the base sheet having its luminous transmittance reduced by the presence of the nonwoven fabric makes it difficult for the helper to visually recognize color change of the core to pale yellow due to urination from the side of the base sheet facing away from the wearer's skin. In this case also, it is apprehended that the helper could not detect from the exterior of the diaper whether urination has occurred or not.

SUMMARY OF THE INVENTION

It is an object of this invention to provide a disposable undergarment enabling a helper to detect whether urination has occurred or not from the exterior of the undergarment even when its base sheet comprises a plastic film and a fibrous nonwoven fabric.

According to this invention, there is provided a disposable undergarment comprising a liquid-impervious base sheet having a wearer's skin side surface and an undergarment side surface and a liquid-absorbent structure lying on the wearer's skin side surface.

The disposable undergarment further comprises that the base sheet comprises a breathable but liquid-impervious inner sheet to define the wearer's skin side surface and a fibrous nonwoven outer sheet joined to the wearer's skin side surface to define the undergarment side surface, and the base sheet having a total luminous transmittance in a range between 60 and 85%.

Embodiments of this invention includes: the liquid-absorbent structure comprises a liquid-absorbent core and a liquid-pervious topsheet covering the core; the inner sheet is formed by an oriented plastic film containing particles of inorganic fillers and has a total luminous transmittance in a range between 65 and 90%; and the outer sheet is made of a nonwoven fabric of thermoplastic synthetic resin and has a basis weight in a range between 10 g/m$^2$ and 50 g/m$^2$ and a surface friction coefficient in a range between 0.05 and 0.3 wherein the synthetic resin fiber has a fineness in a range between 0.01 DTEX and 10 DTEX.

BRIEF DESCRIPTION OF THE DRAWINGS

FIG. 5 is a cross-sectional view taken along a line B—B in FIG. 4.

DETAILED DESCRIPTION OF THE PREFERRED EMBODIMENTS

Details of this invention will be more fully understood from the description of an open-type disposable diaper as one embodiment of this invention given hereunder with reference to the accompanying drawings.

Figure 1:
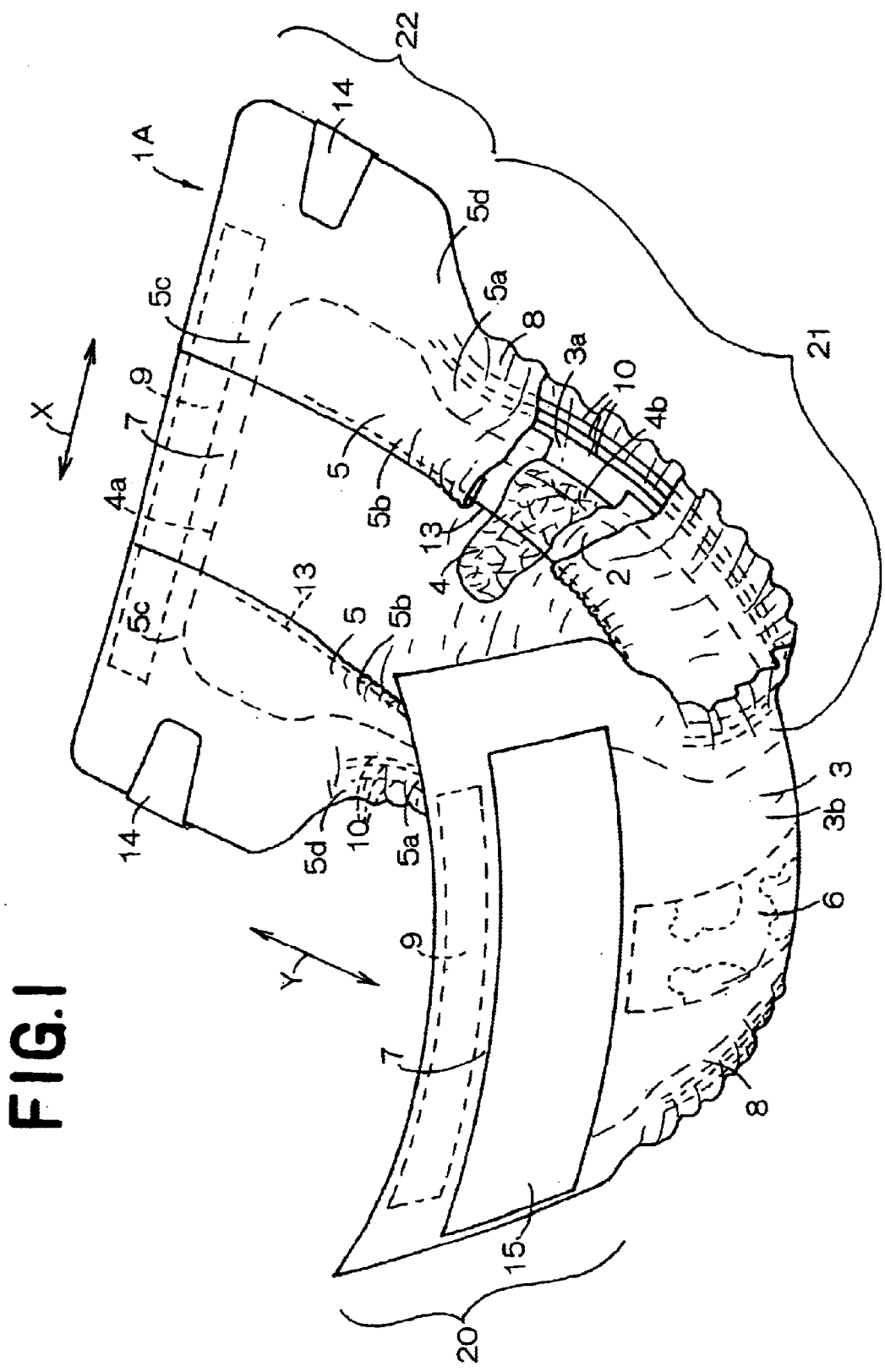
FIG. 1 is a partially cutaway perspective view showing a disposable diaper as viewed from the wearer's skin side thereof.
Figure 2:
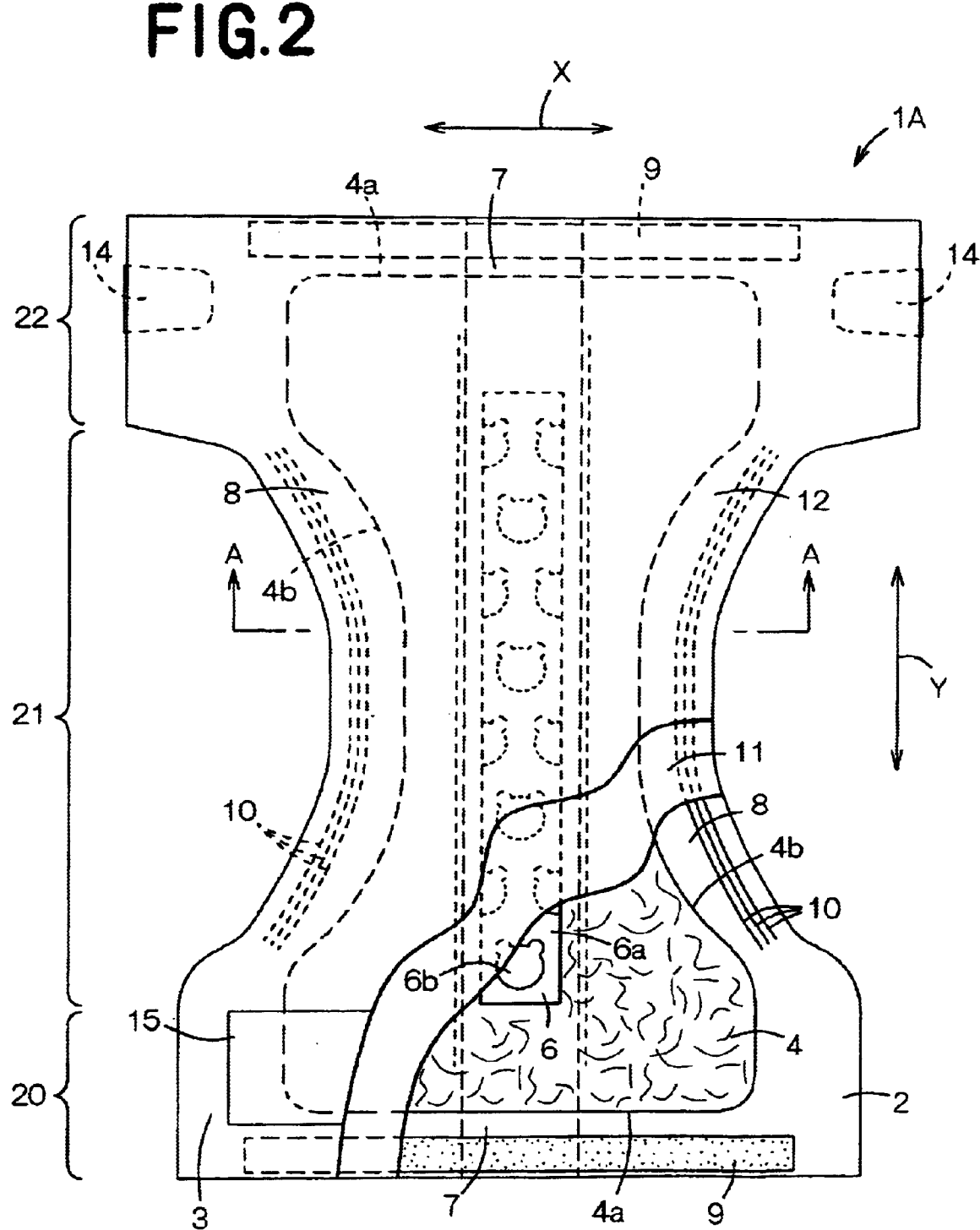
FIG. 2 is a partially cutaway plan view showing the diaper as viewed from the back side thereof.
Figure 3:
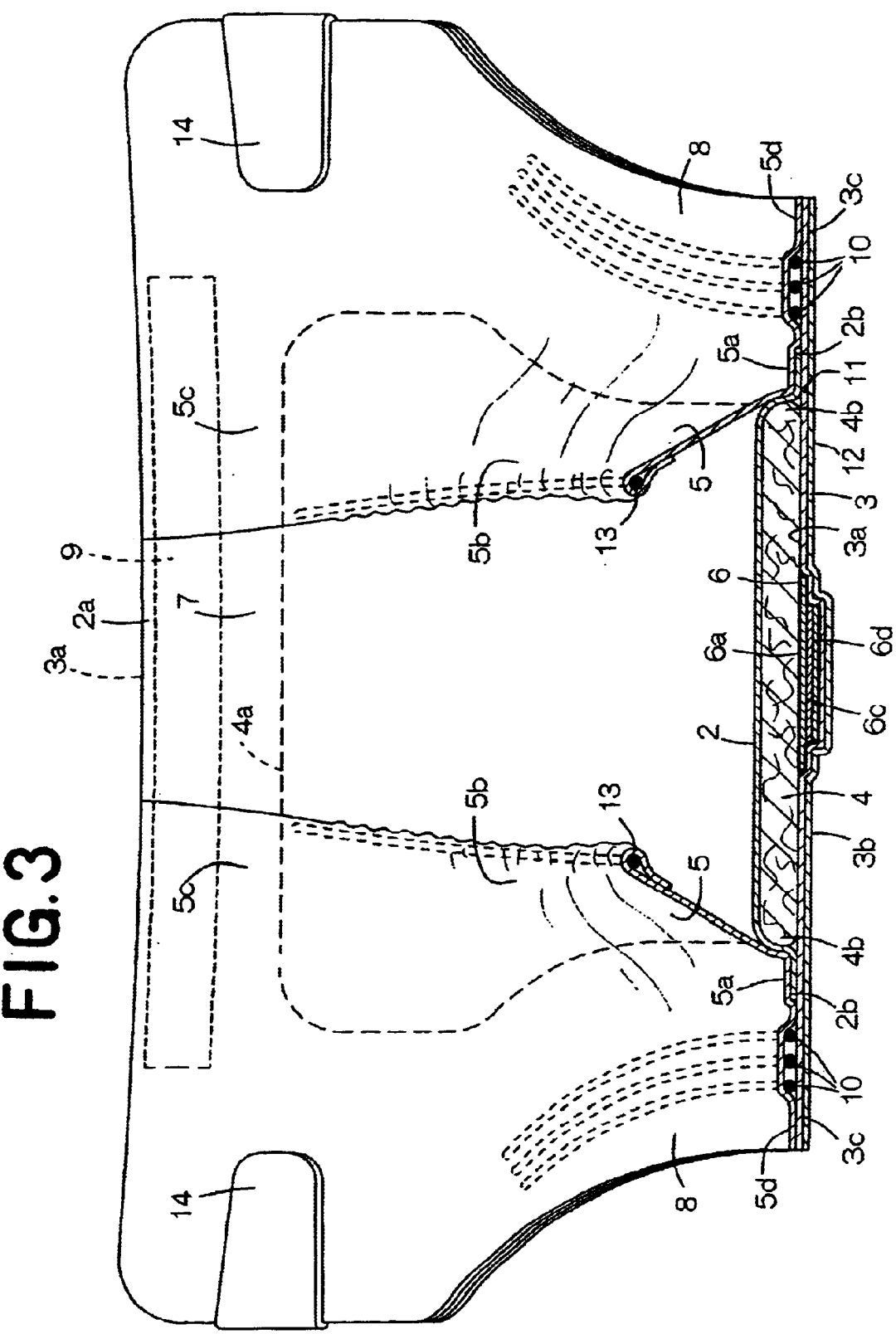
FIG. 3 is a cross-sectional view taken along a line A—A in FIG. 1.

FIG. 1 a partially cutaway perspective view showing a disposable diaper 1 as viewed from the wearer's skin side surface thereof, FIG. 2 is a partially cutaway plan view showing the diaper as viewed from the back side of the diaper and FIG. 3 is a cross-sectional view taken along a line A—A in FIG. 1. In FIGS. 1 and 2, a transverse direction is indicated by an arrow X and a longitudinal direction is indicated by an arrow Y.

A diaper 1A basically comprises a liquid-pervious topsheet 2, a breathable but liquid-impervious base sheet 3 and a liquid-absorbent core 4 disposed between these sheets 2, 3. In addition to these components, the diaper 1A has a pair of substantially liquid-impervious leak-barrier cuffs 5 and a longitudinally elongated indicator 6 enabling a helper to detect whether urination has occurred or not.

Configurationally, the diaper 1A is composed of, in the longitudinal direction, a front waist region 20, a rear waist region 22 and a crotch region 21 positioned between these front and rear waist regions 20, 22. In the diaper 1A, a pair of end flaps 7 extend in the transverse direction outside longitudinally opposite ends 4a of the core 4 and a pair of side flaps 8 extend in the longitudinal direction outside transversely opposite side edges 4b of the core 4. In the crotch region 21, each of the side flaps 8 curves inwardly to the transverse direction of the diaper 1A in a shape of a circular arc, respectively.

Elongated elastic members 9 extending in the transverse direction are attached under extension to the respective end flaps 7 so as to be associated with a waist-hole. In the crotch region 21, a plurality of elastic members 10 extending in the longitudinal direction are attached under extension to the respective side flaps 8 so as to be associated with leg-holes.

The base sheet 3 has a wearer's skin side surface 3a and an undergarment side surface 3b. The base sheet 3 comprises a flexible, breathable but liquid-impervious plastic film 11 defining the wearer's skin side surface and a fibrous non-woven fabric 12 joined to the plastic film 11 defining the undergarment side surface 3b.

The plastic film 11 and the fibrous nonwoven fabric 12 are joined together by means of hot melt adhesive (not shown) applied in a net, or dot, stripe or spiral-like pattern on at least one of these plastic film 11 and fibrous nonwoven fabric 12. Instead of using the hot melt adhesive, another means be used to join the plastic film 11 and the fibrous nonwoven fabric 12 together such as direct laminating, wet laminating or dry laminating technique by extrusion molding.

The core 4 is white- or milky white-colored and entirely covered with and joined to a diffusion sheet such as tissue paper (not shown) and joined to the topsheet 2 as well as to the base sheet 3 with the diffusion sheet disposed therebetween. The core 4 is a mixture of fluff pulp and super-absorbent polymer particles or a mixture of fluff pulp, super-absorbent polymer particles and thermoplastic synthetic resin fiber compressed to a desired thickness.

The leak-barrier cuffs 5 are positioned on the respective side flaps 8 and extend in the longitudinal direction. The cuffs 5 respectively have proximal edge portions 5a extending in the longitudinal direction immediately outside the opposite side edges 4b of the core 4, distal edge portions 5b extending in parallel to the proximal edge portions 5a and normally biased to uprise on the topsheet 2, and fixed longitudinally opposite end portions 5c lying in the front and rear waist regions 20, 22 and collapsed inwardly to the transverse direction of the diaper 1A. Of the cuffs 5, the proximal edge portions 5a are joined to the respective side flaps 8 and the fixed end portions 5c are joined to the respective end flaps 7.

The cuffs 5 further have lateral portions 5d extending outwardly from the respective proximal edge portions 5a in the transverse direction of the diaper 1A. Elastic members 13 extending in the longitudinal direction are attached under extension to the respective free side edge portions 5b. These elastic members 13 are covered with a part of the respective distal edge portions 5b.

The rear waist region 22 is provided with a pair of tape fasteners 14 extending inwardly to the transverse direction of the region 22. The tape fasteners 14 respectively have proximal end portions joined to the respective side flaps 8 of the rear waist region 22. The tape fasteners 14 respectively have free end portions coated with self-adhesive (not shown). In the front waist region 20, a rectangular target tape strip 15 made of a plastics material is joined to the undergarment side surface 3b of the base sheet 3. The target tape strip 15 serves as a landing region for the tape fasteners 14.

The indicator 6 is disposed between the base sheet 3 and the core 4 and extends in the longitudinal direction across a transversely middle zone of the diaper 1A. The indicator 6 is intermittently joined to the base sheet 3 and the core 4 by means of hot melt adhesive (not shown). The indicator 6 comprises a hydrophilic substrate sheet 6a, a first coating layer 6c printed on the outer surface (i.e., the surface opposed to the base sheet 3) of the substrate sheet 6a so as to define a plurality of patterns 6b and a second coating layer 6d covering the first coating layer 6c.

The substrate sheet 6a is formed using a paper sheet having a basis weight in a range between 15 and 40 g/m$^2$. For the first coating layer 6c and the second coating layer 6d, aqueous ink is used. Aqueous ink used for the first coating layer 6c is a mixture of pigment (5–20 wt. %) having a color tone different from those of the substrate sheet 6a and the second coating layer 6d, light scattering inorganic particles (5–35 wt. %) such as silica ($SiO_2$) or alumina ($Al_2O_3$), hydrophilic acrylic binder (5–25 wt. %) and water (30–75 wt. %). The first coating layer 6c appears white so long as the indicator 6 is in a dry state due to random scattering of the light by the inorganic particles, but and becomes distinct as the indicator 6 is wetted with urine as scattering of light is reduced.

Aqueous ink used for the second coating layer 6d is a mixture of light scattering inorganic particles (10–40 wt. %) such as silica ($SiO_2$) or alumina ($Al_2O_3$), hydrophilic acrylic binder (5–25 wt. %) and water (40–85 wt. %) The second coating layer 6d appears white or milky white in a dry state due to random scattering of light and makes it impossible or difficult to visually recognize the first coating layer 6c from the exterior of the diaper 1A so long as the indicator 6 is in a dry state. Once the indicator 6 is wet with urine, the second coating layer 6d becomes transparent due to reduction of random scatteing of light.

In the diaper 1A, the base sheet 3 presents a total luminous transmittance in a range between 60% and 85% as measured in accordance with JIS-K-7105 (Measuring Method A). So far as the total luminous transmittance of the base sheet 3 is in such a range, urine discharged on the diaper 1A and then absorbed by the core 4 permeates into the indicator 6. Specifically, the first coating layer 6c becomes distinct and the second coating layer 6d becomes transparent so that the patterns 6b defined by the first coating layer 6c may be visually recognized through the undergarment side surface 3b of the base sheet 3. The color change of the core 4 from white to pale yellow due to urine permeating into the core 4 can be also visually recognized. In this way, the diaper 1A allows the helper to detect from the exterior of the diaper 1A whether urination has occurred or not.

If the total luminous transmittance of the base sheet 3 is lower than 60%, it would be difficult for the helper to visually detect occurrence of urination through the undergarment side surface 3b of the base sheet 3 even when the first coating layer 6c becomes distinct as this layer 6c is wetted with urine. Furthermore, it would be difficult for the helper to visually recognize the color change of the core 4 through the surface 3b of the base sheet 3 facing away from the wearer's skin.

Monoaxially or biaxially oriented polylefin film containing particles of fine inorganic fillers is preferred as a stock material for the plastic film 11 forming the base sheet 3. The plastic film 11 preferably presents an air permeability rate in a range between 800 and 4000 g/m$^2$·24 hr as measured in accordance with JIS-Z-0208.

Polyolefin resin is preferably selected from a group consisting of polyethylene and polypropylene, more preferably selected from a group consisting of high-density polyethylene, low-density polyethylene and linear low-density polyethylene. The particles inorganic fillers may be selected from a group consisting of particles of calcium carbonate, magnesium carbonate, calcium sulfate, barium sulfate, sodium sulfate and titanium dioxide.

The fibrous nonwoven fabric 12 used as a stock material for the base sheet 3 preferably has a basis weight in a range between 10 g/m² and 50 g/m² and a surface friction coefficient in a range between 0.05 and 0.3 as measured by KES-FB4S manufactured by KATOHTEC Corp.

If the basis weight is lower than 10 g/m², there occurs an anxiety that the strength of the nonwoven fabric might not be strong enough and the nonwoven fabric 12 forming the base sheet 3 might be broken. If the basis weight exceeds 50 g/m², on the contrary, the nonwoven fabric 12 would reduce the total luminous transmittance and make it difficult to ensure the total luminous transmittance of 60% or higher. The surface friction coefficient lower than 0.05 would make a feeling of touch with the nonwoven fabric substantially on the same level as that of the film and make it impossible to improve the feeling of touch with the base sheet 3. If the surface friction coefficient exceeds 0.3, on the contrary, the nonwoven fabric 12 would become sticky like rubber and lose its intrinsic smoothness.

The nonwoven fabric 12 may be selected from a hydrophilic one from a group consisting of those obtained by spun lacing, needle punching, melt blowing, thermal bonding, spun bonding, chemical bonding and air-through processes. The component fiber of the nonwoven fabric 12 may be thermoplastic synthetic resin fiber preferably selected from a group consisting of polyolefin-, polyester- and polyamide-fiber, and more preferably core-sheath type conjugated fiber or side-by-side type conjugated fiber of polyethylene/polypropylene or polyethylene/polyester. While the synthetic resin fiber may contain titanium dioxide ($TiO_2$) so far as the content is less than 2.0 wt %, it is preferable that the synthetic resin fiber does not contain titanium dioxide at all.

The synthetic resin fiber used for this invention preferably has a fineness in a range between 0.01 DTEX and 10 DTEX. The fineness lower than 0.01 DTEX would reduce the strength of the nonwoven fabric 12. The fineness exceeding 10 DTEX would lower the total luminous transmittance of the base sheet 3 through depending on the basis weight of the nonwoven fabric 12.

Referring to FIG. 1, the diaper 1A is curved in the longitudinal direction with the topsheet 2 inside and the free side edge portions 5b of the cuffs 5 rise up on the topsheet as the elastic members 13 contract. With the diaper 1A in this state, the free side edge portions 5b of the cuffs 5 form barriers against body exudates and these barriers serve to prevent the body exudates from leaking sideways beyond the side flaps 8.

In the end flaps 7, the longitudinally opposite end portions 2a of the topsheet 2 and longitudinally opposite end portions 3d of the base sheet 3 extend outwardly in the longitudinal direction beyond longitudinally opposite ends 4a of the core 4 and are overlaid and joined together. The fixed longitudinally opposite end portions 5c of the respective cuffs 5 are bonded to the respective end portions 2a of the topsheet 2. The elastic members 9 associated with the waist-hole are disposed between the end portions 2a of the topsheet 2 and the end portions 3d of the base sheet 3 and joined to these end portions 2a, 3d.

In the side flaps 8, transversely opposite side edge portions 2b of the topsheet 2 extend outwardly in the transverse direction slightly beyond the side edges 4b of the core 4. Transversely opposite side edge portions 3c of the base sheet 3 and transversely opposite side edge portions 5d of the cuffs 5 extend outwardly in the transverse direction beyond the side edge portions 2b of the topsheet 2. The side edge portions 2b are disposed between the side edge portions 3c and the side edge portions 5d, respectively, and joined to these side edge portions 3c, 5d. The side edge portions 3c and the side edge portions 5d are overlaid and joined together. The fixed side edge portions 5a of the respective cuffs 5 are joined to the respective side edge portions 2b of the topsheet 2. The elastic members 10 associated with the leg-holes are disposed between the side edge portions 3c of the base sheet 3 and the side edge portions 5d of the cuffs 5, respectively, and joined to these side edge portions 3c, 5d.

To wear the diaper 1A, the side flaps 8 in the rear waist region 22 are overlaid upon the outer side of the side flaps 8 in the front waist region 20 and then the free end portions of the respective tape fasteners 14 may be anchored on the target tape strip 15 by means of self-adhesive so as to connect the front trunk region 20 with the rear waist region 22. Upon connection of the front and rear waist regions 20, 22 in this manner, the diaper 1A is formed with a waist-hole and a pair of leg-holes.

It is not essential to attach the indicator 6 to the diaper 1A shown in FIG. 1. This is because so far as the total luminous transmittance of the base sheet 3 is in the above-specified range, the color change of the core 4 to pale yellow due to urination can be visually recognizable through the undergarment side surface 3b of the base sheet 3. In this way, the helper can detect from the exterior of the diaper 1A whether urination has occurred or not even if the diaper 1A is not provided with the indicator 6.

Figure 4:
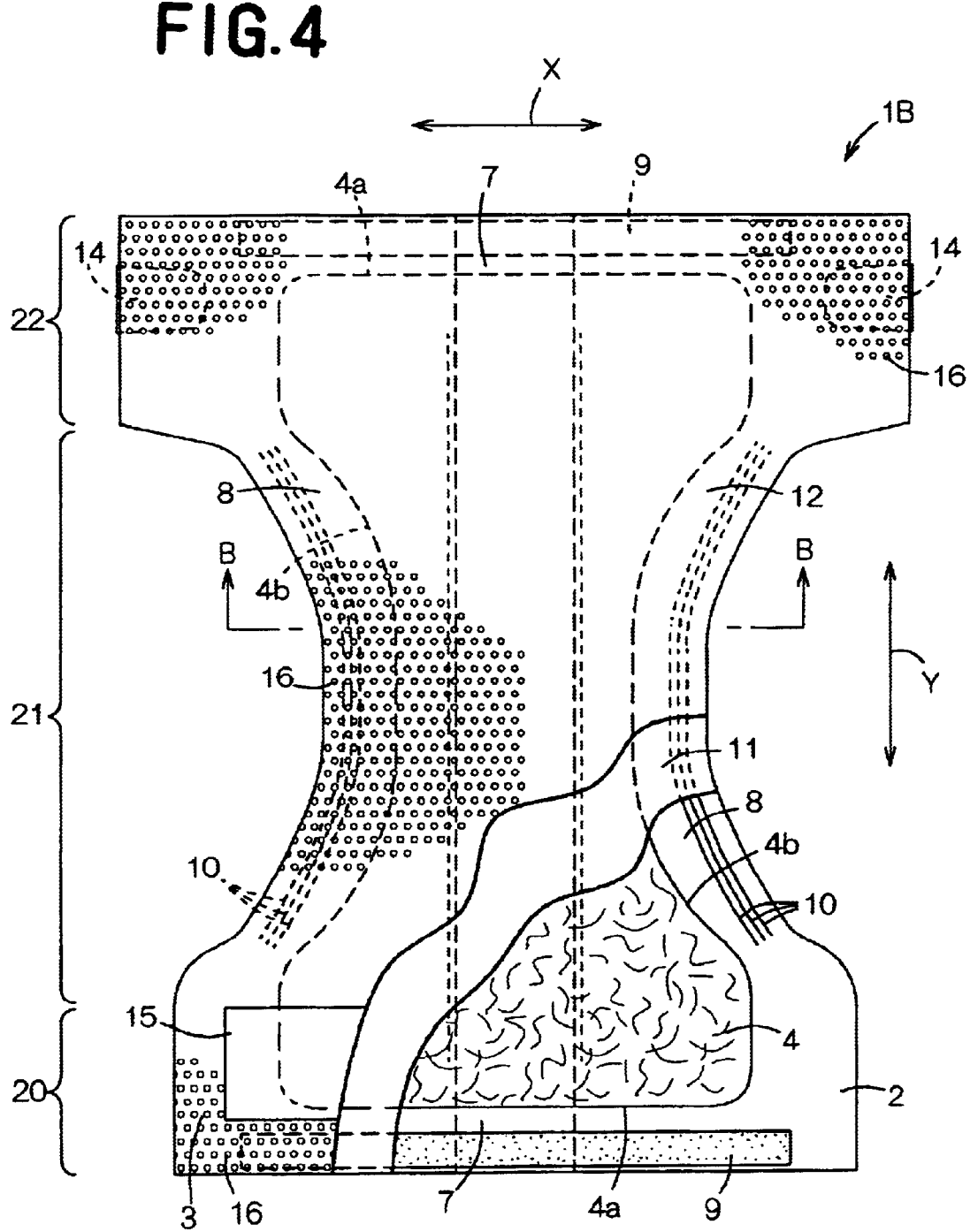
FIG. 4 is a partially cutaway plan view similar to FIG. 2 but showing an alternative embodiment of the diaper.

FIG. 4 is a partially cutaway plan view showing a diaper 1B according to an alternative embodiment as viewed from the side of the base sheet 3 and FIG. 5 is a cross-sectional view taken along a line B—B in FIG. 4. This diaper 1B is distinguished from the diaper 1A shown in FIG. 1 in that the diaper 1B is not provided with an indicator and the base sheet 3 has an embossed region 16 defined by a plurality of embossed dots.

Similarly to the base sheet 3 shown in FIG. 1, the base sheet 3 comprises a flexible, breathable but liquid-impervious plastic film 11 which defines the wearer's skin side surface 3a and the fibrous nonwoven fabric 12 joined to the plastic film 11 to define the undergarment side surface 3b.

The plastic film 11 and the fibrous nonwoven fabric 12 may be similar to those shown in FIG. 1. The plastic film 11 and the fibrous nonwoven fabric 12 are joined together by means of hot melt adhesive applied to at least one of them and, in the embossed region, the plastic film 11 and the fibrous nonwoven fabric 12 are heat welded together.

The base sheet 3 in the embossed region 16 has a total luminous transmittance in a range between 65% and 85%. In the embossed region 16, the fibrous nonwoven fabric 12 becomes film-like thin and the total luminous transmittance of the base sheet 3 is correspondingly higher in this embossed region 16 than the remaining region.

A ratio of the area of the embossed region 16 to the total area of the base sheet 3 is preferably in a range between 5 and 50% If this area ratio of the embossed region 16 exceeds 50%, it would increase a stiffness of the base sheet 3 and reduce a desired feeling of touch with the sheet 3.

In the case of this diaper 1B, the base sheet 3 as a whole preferably has a total luminous transmittance in a range between 60 and 85%. With the diaper 1B, the color change to pale yellow occurring in the core 4 due to urination can be visually recognizable through the surface 3b of the base sheet 3 facing away from the wearer's skin, so that it can be detected from the exterior of the diaper 1B whether urination has occurred or not. With the diaper 1B shown in FIG. 3, it is also possible to emboss the fibrous nonwoven fabric 12 alone to form the embossed region 16.

Both the diaper 1A and the diaper 1B shown in FIGS. 1 and 3, respectively, preferably have bending resistance in a range between 15 and 65 mm as measured in accordance with JIS-L-1018 (cantilever method).

The topsheet 2 may be formed from hydrophilic fibrous nonwoven fabric or plastic film with fine pores. The leak-barrier cuffs 5 may be formed from a hydrophobic fibrous nonwoven fabric. The nonwoven fabric forming the topsheet 2 and the cuffs 5 may be selected from a group consisting of those obtained by spun lacing, needle punching, melt blowing, thermal bonding, spun bonding, chemical bonding and air-through processes.

Joining between the topsheet 2 and the base sheet 3, fixing of the leak-barrier cuffs 5, joining of the core 4, and attachment of the respective elastic members 9, 10, 13 may be achieved using hot melt adhesive or heat welding technique such as heat-sealing or ultrasonic-sealing.

This invention is applicable not only to an open-type diaper but also to a pants-type diaper having its front and rear trunk regions previously connected to each other.

In the disposable undergarment according to this invention, as the base sheet has the total luminous transmittance in a range between 60 and 85%, the color change to pale yellow occurring in the core due to urination is visually recognizable through the undergarment side surface of the base sheet so that it can be detected from the exterior of the article whether urination has occurred or not.

This article has the advantages in that the base sheet comprises the breathable but liquid-impervious plastic film and the hydrophobic fibrous nonwoven fabric. Such a unique arrangement enables a feeling of touch with the base sheet to be improved in comparison to the case in which the base sheet is formed by the plastic film alone.

What is claimed is:

1. A disposable undergarment comprising:
    a liquid-impervious base sheet having a skin side surface and an undergarment side surface;
    a liquid-absorbent structure lying on the skin side surface of said base sheet; and
    said base sheet comprising a breathable but liquid-impervious inner sheet that defines said skin side surface and a fibrous nonwoven outer sheet joined to said inner sheet that defines said undergarment side surface, said base sheet having a total luminous transmittance in a range of between 60 and 85%.

2. The undergarment according to claim 1, wherein said liquid-absorbent structure comprises a liquid-absorbent core and the disposable undergarment further comprises a liquid-pervious topsheet covering an upper surface of said core.

3. The undergarment according to claim 1, wherein said inner sheet comprises a plastic film containing particles of inorganic fillers and having a total luminous transmittance in a range between 65 and 90%.

4. The undergarment according to claim 1, wherein said nonwoven outer sheet comprises a nonwoven fabric of thermoplastic synthetic resin fiber that has a basis weight in a range of between 10 $g/m^2$ and 50 $g/m^2$ and a surface friction coefficient in a range between 0.005 and 0.3 and wherein said synthetic resin fibers have a fineness in a range between 0.01 DTEX and 10 DTEX.

5. The undergarment according to claim 1, wherein said undergarment further comprises a longitudinally elongated indicator disposed between and intermittently joined to said base sheet and said absorbent structure.

6. The undergarment according to claim 5, wherein said indicator comprises a hydrophilic substrate sheet, a first coating layer printed on a surface of said substrate that is opposed to said base sheet so as to define a pattern and a second coating layer covering said first coating layer, wherein an aqueous ink is used for both said first and second coating layer and said aqueous ink used for said first coating layer is a mixture of pigment having a color tone different from said substrate sheet and said second coating layer, light scattering inorganic particles, a hydrophilic acrylic binder and water.

7. The undergarment according to claim 3, wherein said base sheet comprises an embossed region in which said fibrous nonwoven fabric is thin as a film.

* * * * *